United States Patent [19]
Drasner et al.

[11] Patent Number: 5,234,406
[45] Date of Patent: Aug. 10, 1993

[54] METHOD AND SYSTEM FOR CONTINUOUS SPINAL DELIVERY OF ANESTHETICS

[75] Inventors: Kenneth Drasner; Mark L. Rigler, both of San Francisco, Calif.

[73] Assignee: The Regents of the University of California, Oakland, Calif.

[21] Appl. No.: 864,296

[22] Filed: Apr. 6, 1992

[51] Int. Cl.$^5$ ............................................. A61M 5/00
[52] U.S. Cl. ........................................ 604/51; 604/80; 604/264
[58] Field of Search ................ 604/51, 80, 81, 43–45, 604/53, 272, 273, 264, 280, 282, 283; 128/657, 658, 778

[56] References Cited

U.S. PATENT DOCUMENTS

| | | | |
|---|---|---|---|
| 2,710,004 | 6/1955 | Stamper | 604/80 |
| 4,737,146 | 4/1988 | Amaki et al. | 604/51 |
| 4,917,670 | 4/1990 | Hurley et al. | 604/51 |

OTHER PUBLICATIONS

Greene (1985) Anesth. Analg. 64:715–730.

*Primary Examiner*—John D. Yasko
*Attorney, Agent, or Firm*—Townsend and Townsend Khourie and Crew

[57] ABSTRACT

The catheter system for delivering an anesthetic solution to the subarachnoid space of a patient comprises a small diameter catheter section joined to a larger diameter extension tube. The small diameter catheter section is introduced to the subarachnoid space, typically using an introducer needle, and anesthetic can be delivered to the catheter section through the large diameter tube extension. In this way, total flow resistance to the delivery of the anesthetic is reduced without the corresponding increase in the portion of the catheter which is introduced to the subarachnoid space.

18 Claims, 3 Drawing Sheets

METHOD AND SYSTEM FOR CONTINUOUS SPINAL DELIVERY OF ANESTHETICS

BACKGROUND OF THE INVENTION

1. Field of the Invention

The present invention relates generally to methods and systems for patient anesthesia, and more particularly to methods and systems for the spinal delivery of anesthetics.

Spinal anesthetics are useful for many abdominal, pelvic, and lower extremity surgical procedures which require only local anesthesia. Spinal anesthesia is achieved by injecting a local anesthetic into the subarachnoid space between adjacent vertebrae in the lumbar region. While extremely useful, the effect and duration of spinal anesthesia is unpredictable and difficult to control.

Spinal anesthetics may be injected in a single dosage using a hypodermic syringe or may be administered in multiple dosages using a catheter which remains attached to the patient during the entire course of a surgical procedure. Such continuous administration of the spinal anesthetic helps assure extended anesthesia over longer periods of time. Heretofore, relatively large diameter catheters have been used for the continuous administration of spinal anesthetics. The large diameter, typically in the range from about 20 gauge to 24 gauge, has been employed primarily due to availability and ease of use. The use of larger diameter catheters, however, is undesirable since the larger diameter increases the chances of injury to the patient, particularly causing a greater incidence of postdural headaches.

For these reasons, it would be desirable to provide improved methods and systems for the continuous and intermittent administration of anesthetics to the subarachnoid space. In particular, it would be desirable to provide such methods and systems which permit continuous delivery of the anesthetic at relatively high injection rates without the need to introduce a relatively large diameter catheter to the subarachnoid space.

2. Description of the Background Art

Greene (1985) Anesth. Analg. 65:715-730, is a review article describing the effect of various factors on the distribution of spinal anesthetics in the subarachnoid space. In particular, the effect of the technique of injection is discussed on pp. 718-720.

SUMMARY OF THE INVENTION

The present invention provides improved methods and systems for the continuous or intermittent delivery of anesthetic solutions to the subarachnoid space of a patient. The methods comprise introducing a distal end of a small diameter catheter to the subarachnoid space, typically through a previously positioned needle. The anesthetic solution is then delivered through a large diameter tube to the proximal end of the small diameter catheter. By limiting the length of the small diameter catheter, typically to a length in the range from about 15 cm to 25 cm, and relying on the large diameter tube for access to the patient, the flow resistance to the anesthetic is significantly reduced. The patient, however, is exposed only to the small diameter catheter, thus limiting the risk of postdural headaches and other adverse side effects.

The catheter system of the present invention comprises a small diameter catheter section having a proximal end, a distal end, and a lumen therethrough. The small diameter catheter section has an outside diameter of 26 gauge, or smaller, and a total length usually in the range from about 15 cm to 25 cm. The system further comprises a large diameter tube having a proximal end, a distal end, a lumen therethrough, and a diameter of 24 gauge or larger. In a preferred system, the catheter section will have a diameter of 28 gauge or smaller and the tube will have a diameter of 22 gauge or larger. The distal end of the large diameter tube is secured to the proximal end of the small diameter catheter, either detachably or permanently, so that their respective lumens are joined and anesthetic may be delivered from the proximal end of the tube to the distal end of the small diameter catheter section. Preferably, the distal end of the catheter is tapered, and optionally the distal end may include one or more laterally exposed distribution ports. In a particular aspect of the present invention, the distribution ports at the distal end of the catheter have a total cross-sectional area less than that of the catheter lumen. In this way, exit velocity of the anesthetic solution from the distribution port(s) is increased to enhance distribution within the subarachnoid space. Preferably, the catheter is secured to the tube with a flat hub structure which can facilitate taping of the catheter system to the patient's skin.

DESCRIPTION OF SPECIFIC EMBODIMENTS

Figure 1:
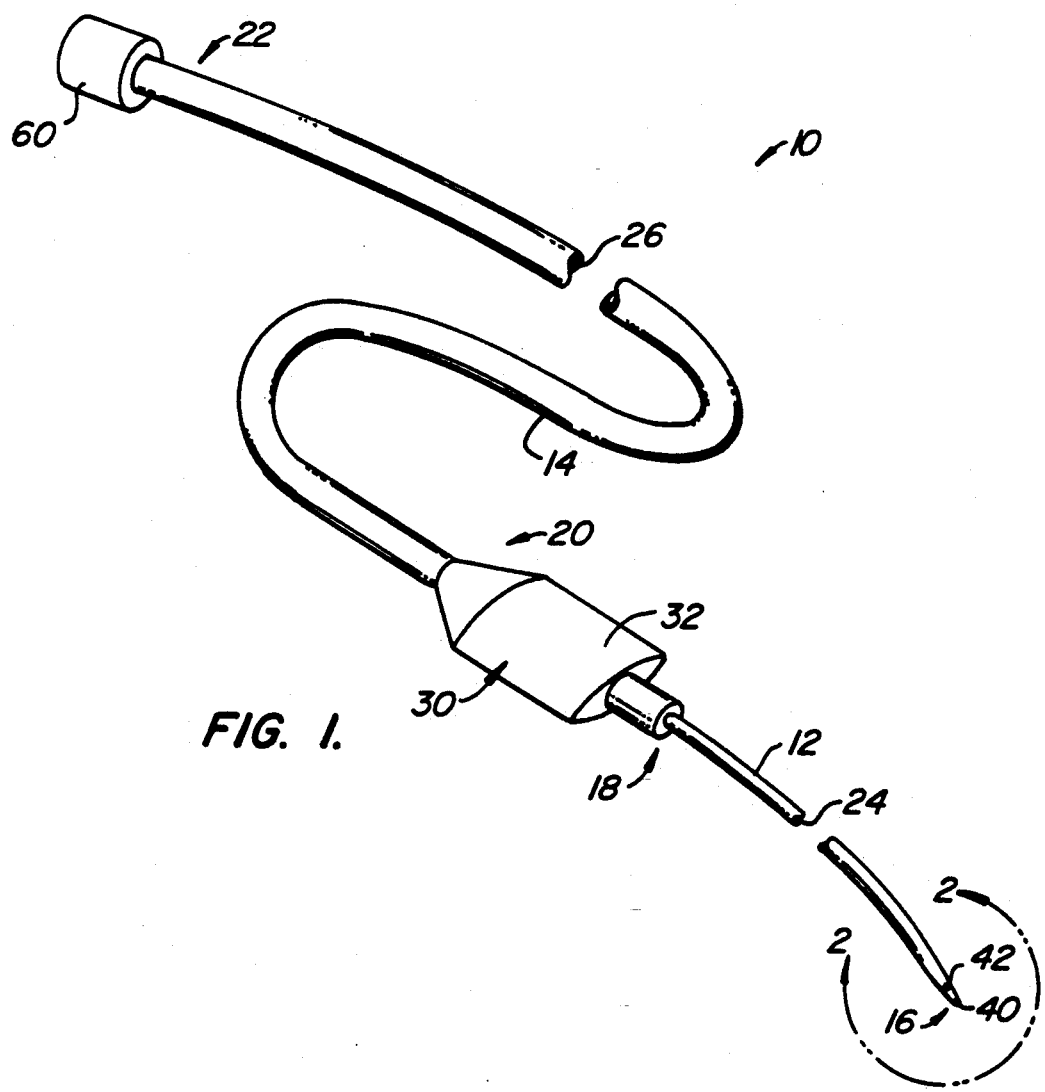
FIG. 1 is a perspective view of a catheter system constructed in accordance with the principles of the present invention.

A catheter system 10 constructed in accordance with the principles of the present invention includes a distal catheter section 12 and a proximal tube extension section 14. The distal catheter section 12 has a distal end 16 and a proximal end 18, while the proximal extension tube section 14 includes a distal end 20 and a proximal end 22. A small diameter lumen 24 extends between the proximal end 16 and distal end 18 of the distal catheter section 12, and a larger diameter lumen 26 extends between the distal end 20 and the proximal end 22 of the proximal extension tube section 14. A connector hub 30 provides a transition or connection between the catheter section 12 and tube section 14, and in particular joins the lumen 24 and the lumen 26 so that anesthetic solution introduced through the tube section 14 can flow into the catheter section 12 with minimal flow resistance. The connection provided by hub 30 can be permanent, i.e. joined together by an adhesive, heat welding, or the like, or may be detachable, i.e. joined together by an impermanent connector, such as a layer fitting, threaded connection, bayonet connection, or the like. As illustrated, hub 30 has a low profile (relatively flat opposed surfaces 32) which facilitates placement and optional taping of the hub against a patient's skin, as described below. Usually, the hub 30 will be covered with padding (not illustrated) to protect the patient.

It will be appreciated that a wide variety of other transition regions could be provided between the catheter section 12 and extension tube section 14. Most simply, the tubes could be formed from a single extrusion, with the proximal tube section 14 being expanded relative to the distal catheter section 12. The only requirement of the transition is that the larger diameter lumen 26 in the tube section 14 be fluidly coupled to the smaller diameter lumen 24 in the catheter section 12, with the transition usually providing minimum flow resistance.

The distal catheter section 12 will be a flexible tube, usually being composed of an organic polymeric material, such as nylon, polyimide, polytetrafluoroethylene (PTFE; Teflon TM), polyurethane, or the like. A wide variety of suitable organic polymers which can be extruded and formed into the desired tube geometry are available. The tube of the distal catheter section 12 should have sufficient stiffness to permit insertion into the subarachnoid space (as described hereinafter) and to maintain patency of lumen 24, but should also be sufficiently soft and flexible to permit bending and to reduce trauma when inserted to the subarachnoid space. Typically, the polymer will have a hardness in the range from about 40A to 60D. It would also be possible, however, to form the distal catheter section 12 from a malleable metal, although this would generally not be preferred.

The distal catheter section 12 will have a small lumen diameter, typically being from 28 gauge to 32 gauge, and will have a length in the range from about 15 cm to 25 cm, usually in the range from 18 cm to 20 cm. It should be appreciated that the length of the distal catheter section 12 will generally be minimized in order to reduce flow resistance. Lengths in the ranges set forth above are generally long enough to accommodate insertion through a conventional spinal needle, with minimum excess length.

Figure 2:
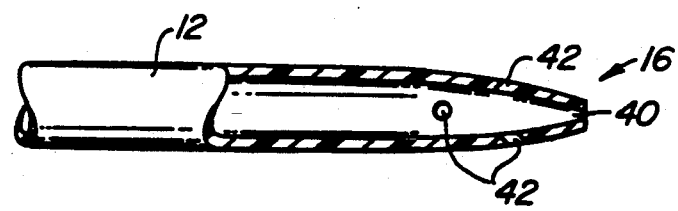
FIG. 2 is a detailed view of the distal tip portion of the catheter of FIG. 1, taken at line 2—2 and shown in partial section.
Figure 3:
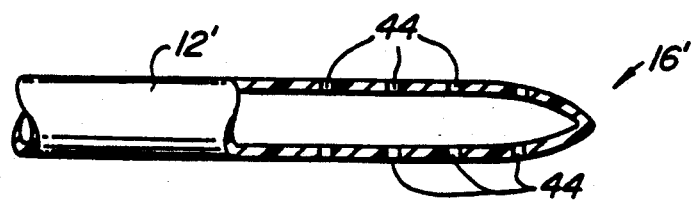
FIG. 3 is a partial sectional view of an alternate configuration of the distal tip of the catheter of FIG. 1.

The distal tip 16 of the distal catheter section 12 will usually be tapered and will include one or more distribution ports, with a distal tip distribution port 40 and one or more laterally disposed or side distribution ports 42 being illustrated in FIGS. 1 and 2. The diameter of the distribution ports may vary, typically being from about 1 $\mu$m to 150 $\mu$m, usually being from about 10 $\mu$m to 100 $\mu$m. An alternative configuration of the distal tip 16' is illustrated in FIG. 3. Distal catheter section 12' terminates in a closed, tapered structure (i.e. no distal tip distribution port) and includes a plurality of side ports 44. The number of side ports 44 can vary widely, from several to as many as 100, or more. In the case of a large number of side ports 44, the diameter of the individual side distribution ports will typically be smaller, usually being below 10 $\mu$m, and frequently being below 1 $\mu$m. Such smaller distribution ports can conveniently be formed by laser drilling.

In a preferred aspect of the present invention, the total area of all distribution ports will be less than that of the cross-sectional area of the catheter section lumen 24. Reducing the distribution port area relative to the lumen area creates a nozzle effect, where the anesthetic solution flow velocity through the distribution ports is increased. It is believed that such increased flow velocity improves the distribution of the anesthetic within the subarachnoid space. Usually, the area of lumen 24 will be in the range from $10^4$ $\mu m^2$ to $5 \times 10^4$ $\mu m^2$, and the total distribution port area will usually be from about 50% to 75% of the lumen area. Too great a reduction in the distribution port area will cause an undesirable increase in the flow resistance, and thus should be avoided.

The proximal extension tube 14 will usually be composed of polymeric material, typically being nylon, polyimide, PTFE, polyurethane, or the like, as described above for the distal catheter section 12. Conveniently, the proximal tube section 14 will be composed of the same material as the distal catheter section 12, but such identity of materials is not necessary. The length of the proximal tube section 14 will usually be from about 50 cm to 100 cm, more usually being from about 65 cm to 75 cm. The diameter of lumen 26 in the proximal tube section 14 will be greater than that of lumen 24, usually being from 20 to 22 gauge. By providing such larger lumen diameters, the total flow resistance of the catheter system 10 is reduced, facilitating introduction of the anesthetic solution, as described below. While it would be possible to increase the diameter of lumen 26 even further, such larger lumen diameters in the proximal tube section 14 can cause an undesirable increase in the total void volume of the catheter. Such void volume lessens the accuracy of volumetric delivery and represents a waste of the anesthetic, and is thus undesirable. The catheter systems 10 of the present invention will typically have a void volume in the range from about 0.1 ml to 0.3 ml.

Referring now to FIGS. 4A–4D, the method of the present invention will be described. Initially, an introducing needle 50 is percutaneously introduced to the subarachnoid space SA. Needle 50 will be introduced between adjacent vertebrae, usually between L2 and L3, or below. See FIG. 4A.

Figure 4A:
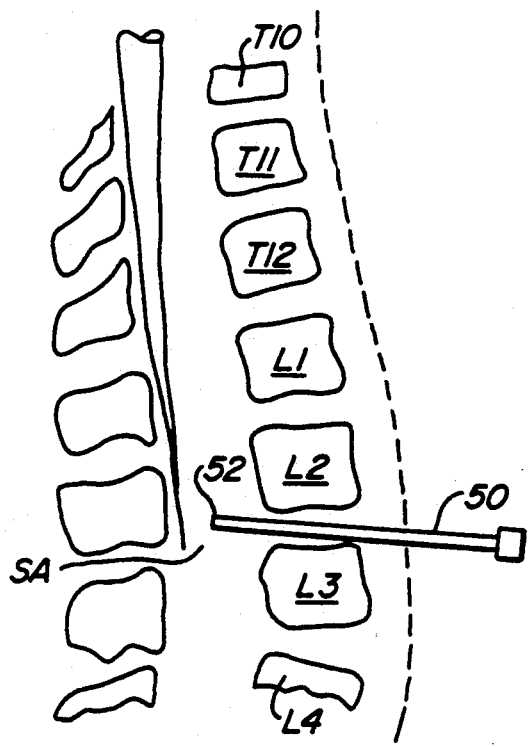
FIGS. 4A-4D illustrate use of the catheter of FIG. 1 in the method of the present invention.
Figure 4B:
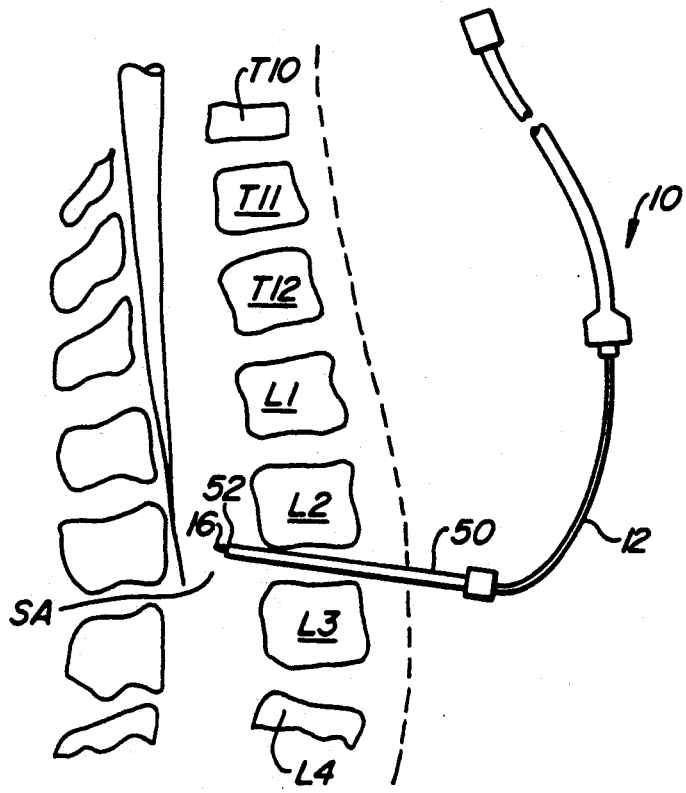
Figure 4C:
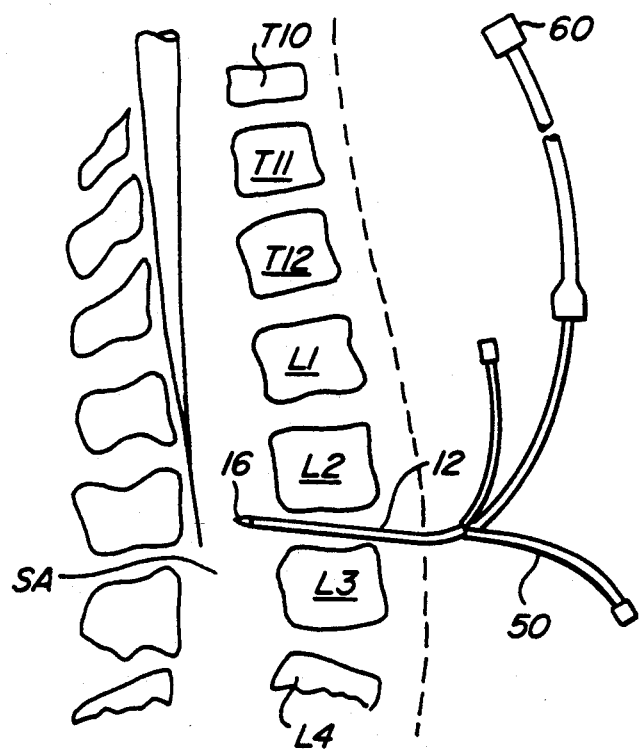

After the distal tip 52 of needle 50 has reached the subarachnoid space SA, the distal catheter section 12 of catheter system 10 is introduced through the lumen of the needle, as illustrated in FIG. 4B. The catheter section 12 is introduced sufficiently far so that its distal end 16 at least reaches and usually extends beyond the distal tip 52 of needle 50 by up to about 6 cm. After the catheter section 12 has been fully introduced, the needle 50 is withdrawn, and optionally split apart, as illustrated in FIG. 4C. The method of the present invention, however, could also utilize other types of needles which are withdrawn over or are protected and remain in place over the distal catheter section 12 during subsequent use.

Figure 4D:
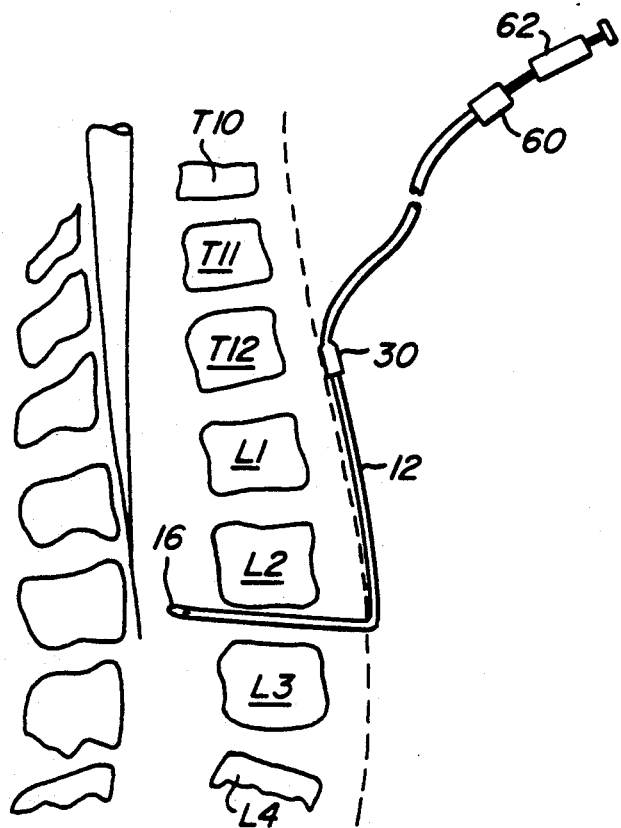

In any event, after the needle 50 has been withdrawn, the distal catheter section 12 will usually be folded over onto the patient's back, with the hub 30 being taped in place, as illustrated in FIG. 4D. A syringe hub 60 at the proximal end of the extension tube section 14 will be brought around the patient (with the patient typically lying on his or her back) and will be available for injection of a desired anesthetic solution.

Suitable anesthetics include local anesthetics, such as procaine, tetracaine, dibucaine, lidocaine, and the like. The anesthetic solutions will be introduced through the syringe hub 60 using a conventional syringe 62. Dosages will depend on the nature and length of the procedure, typically being from 1 ml to 3 ml, with a total of from 1 to 10 injections being given during the course of the procedures.

A particular advantage of the present invention is that the injections of the anesthetic solution can be made over a relatively short time frame, typically 5 seconds to 30 seconds, with good distribution of the anesthetic solution within the subarachnoid space being achieved. Use of conventional narrow diameter catheters for such injection is more difficult and results in a lesser distribution of the anesthetic within the subarachnoid space.

Although the foregoing invention has been described in detail for purposes of clarity of understanding, it will be obvious that certain modifications may be practiced within the scope of the appended claims.

We claim:

1. A method for delivering an anesthetic solution to the subarachnoid space of a patient, said method comprising:

introducing a distal end of a small diameter catheter to the subarachnoid space between adjacent vertebrae; and delivering the anesthetic solution through a large diameter tube to a proximal end of the small diameter catheter, wherein the length of the large diameter tube is greater than that of the small diameter catheter whereby fluid flow resistance through the combined tube and catheter is reduced and anesthetic delivery rate to the subarachnoid space is enhanced.

2. A method as in claim 1, wherein the diameter of the small diameter catheter is 26 gauge or smaller and the diameter of the large diameter tube is 24 gauge or larger.

3. A method as in claim 1, wherein the anesthetic solution is delivered in a plurality of injection of 1 ml to 3 ml in the proximal end of the tube.

4. A method as in claim 1, further comprising taping a junction between the small diameter catheter and the large diameter tube to the patient's skin prior to delivering the anesthetic.

5. A method for delivering an anesthetic solution to the subarachnoid space of a patient, said method comprising:

percutaneously positioning a distal end of a needle in the subarachnoid space between adjacent vertebrae;

introducing a distal end of a small diameter catheter having a length in the range from 15 cm to 25 cm through the needle to the subarachnoid space;

withdrawing the needle at least partially from the subarachnoid space while leaving the catheter in place; and delivering the anesthetic solution through a large diameter tube having a length in the range from 50 cm to 100 cm to a proximal end of the small diameter catheter, whereby fluid flow resistance through the combined tube and catheter is reduced and anesthetic delivery rate to the subarachnoid space is enhanced.

6. A method as in claim 5, wherein the diameter of the small diameter catheter is 28 gauge or smaller and the diameter of the large diameter tube is 22 gauge or larger.

7. A method as in claim 5, wherein the anesthetic solution is delivered in a plurality of injection of 1 ml to 3 ml in the proximal end of the tube.

8. A method as in claim 5, further comprising taping a junction between the small diameter catheter and the large diameter tube to the patient's skin prior to delivering the anesthetic.

9. A catheter system for delivering an anesthetic solution to the subarachnoid space of a patient, said system comprising:

a small diameter catheter having a proximal end, a distal end, a lumen therethrough, at least one distribution port at the distal end, and a diameter of 26 gauge or smaller;

a large diameter tube having a proximal end, a distal end, a lumen therethrough, and a diameter of 24 gauge or larger, wherein the length of the large diameter tube is greater than that of the small diameter catheter; and means for securing the distal end of the large diameter tube to the proximal end of the small diameter catheter, whereby their respective lumens are joined and anesthetic delivery rate through the catheter is enhanced.

10. A catheter system as in claim 9, wherein the distal end of the small diameter catheter is tapered.

11. A catheter system as in claim 9, wherein the small diameter catheter includes at least one laterally disposed distribution port.

12. A catheter system as in claim 9, wherein the distribution ports have a total cross-sectional area less than that of the small diameter catheter lumen.

13. A catheter system as in claim 9, wherein the means for securing the tube to the catheter is permanent.

14. A catheter system as in claim 9, wherein the means for securing the tube to the catheter is detachable.

15. A catheter system as in claim 9, wherein the means for securing the tube to the catheter comprises a flat hub to facilitate taping to the patient's skin.

16. A catheter system as in claim 9, wherein the large diameter tube includes means at its proximal end for detachably securing to a source of anesthetic solution.

17. A catheter system as in claim 9, wherein the small diameter catheter has a length in the range from 15 cm to 25 cm.

18. A catheter system as in claim 17, wherein the large diameter tube has a length in the range 50 cm to 100 cm.

* * * * *